United States Patent [19]

Johnson et al.

[11] Patent Number: 4,786,631

[45] Date of Patent: Nov. 22, 1988

[54] NOVEL ARGININE VASOPRESSIN-BINDING PEPTIDES

[75] Inventors: Howard M. Johnson; Barbara A. Torres, both of Gainesville, Fla.

[73] Assignee: University of Florida, Gainesville, Fla.

[21] Appl. No.: 169,713

[22] Filed: Mar. 18, 1988

[51] Int. Cl.[4] ........................ A61K 37/34; C07K 7/06; C07K 7/16

[52] U.S. Cl. ........................................ 514/15; 530/328; 530/315; 514/807

[58] Field of Search ........................ 530/315, 316, 328; 514/15, 807

[56] References Cited

U.S. PATENT DOCUMENTS

| | | | |
|---|---|---|---|
| 3,980,631 | 9/1976 | Prochazka et al. | 530/315 |
| 4,714,696 | 12/1987 | Manning et al. | 530/315 |
| 4,719,199 | 1/1988 | Yim | 514/10 |
| 4,724,229 | 2/1988 | Ali | 530/315 |
| 4,742,154 | 5/1988 | Bryan et al. | 530/315 |

*Primary Examiner*—Delbert R. Phillips
*Assistant Examiner*—T. D. Wessendorf
*Attorney, Agent, or Firm*—Roman Saliwanchik; David R. Saliwanchik

[57] ABSTRACT

The invention concerns novel AVP-binding peptides having the formula:

Thr-Met-X-Val-Leu-Thr-Gly-Ser-Pro-B wherein X is selected from the group consisting of Lys, Arg, and Asp; B is OH, $NH_2$, NHAlk, wherein Alk is lower alkyl of 1–4 carbons, inclusive. These peptides block AVP function, and, therefore, are useful in many areas among which is the control of hypertension.

8 Claims, 1 Drawing Sheet

NOVEL ARGININE VASOPRESSIN-BINDING PEPTIDES

The work disclosed herein was supported, in part, by Grant CA39048 from the National Institutes of Health.

BACKGROUND OF THE INVENTION

Arginine vasopressin (AVP) is a neurohypophyseal (posterior pituitary) nonapeptide that plays an important regulatory role in individuals with respect to a number of functions. These include: (a) antidiuretic effects by acting on specific receptors in the kidney; (b) vasopressor effects which, in concert with other peptide hormones, regulate systemic arterial pressure; (c) modulation of the stress response by direct stimulation of release of corticotropin (ACTH) and by enhancement of ACTH release by corticotropin releasing factor; (d) enhancement of learning and memory; (e) functioning as a neurotransmitter; and (f) positive regulation of immune function by providing a helper signal for induction of the lymphokine gamma interferon (IFN γ) (Johnson, H. M., W. L. Farrar, and B. A. Torres [1982] J. Immunol. 129:963; and Johnson, H. M. and B. A. Torres [1985] J. Immunol. 135:773s). To date the sole approach to modulation of AVP activity has been through the use of competitive antagonists for receptors (Manning, M. and Sawyer, W. H. in *Vasopressin* [ed. Schrier, R. W.] 131-144, Raven Press, New York, 1985; and Stassen, F. L., Heckman, G. D., Schmidt, D. B., Stefankiewicz, J., Sulat, L., Huffman, W. F., Moore, M. M., and Kinter, L. B. in *Vasopressin* [ed. Schrier, R. W.] 145-154, Raven Press, New York, 1985).

Recently issued U.S. Pat. No. 4,597,901 is directed to "β-Indolyalanyl or β-Indolylglycinyl Vasopressin Antagonists," and U.S. Pat. No. 4,719,199 is directed to "Diuretic Compositions and Methods of Producing Diuresis." The latter patent results from a divisional application of the former patent. These patents disclose AVP antagonists and their use as diuretics.

BRIEF SUMMARY OF THE INVENTION

The subject invention concerns novel AVP-binding peptides having the formula:

Thr-Met-X-Val-Leu-Thr-Gly-Ser-Pro-B wherein X is selected from the group consisting of Lys, Arg, and Asp; B is OH, $NH_2$ or NHAlk. "Alk" is lower alkyl of 1-4 carbons, inclusive. Advantageously, the novel peptides of the invention bind to AVP and block AVP function. The AVP-binding peptides of the invention differ from AVP analogs that have been previously synthesized. The AVP antagonists that have been synthesized to date all block AVP activity through direct interaction with the AVP cellular receptor. On the other hand, the AVP-binding peptides of the invention block AVP activity by actually binding to AVP itself. Thus the interaction of AVP binding peptides with AVP results in an antagonist of AVP action.

The AVP-binding peptides of the subject invention can be used to block both antidiuretic and vasopressor activities, resulting in decreased blood volume and decreased blood pressure. Accordingly, the AVP-binding peptides of the invention would be useful in the control of hypertension. The AVP-binding peptides also can be used in the down-regulation of AVP-modulated immune responses. This would be important for the treatment of allergic disorders and immune complex diseases. AVP-binding peptides may also help control or reduce the stress response by decreasing the release of corticotrophin. Thus, the AVP-binding peptides may be powerful therapeutic tools for the control of AVP-modulated physiologic responses.

The AVP-binding peptides can be used in a solid-matrix binding assay in which AVP specifically competes with $^3H$-AVP for binding to immobilized AVP-binding peptide. This is useful for the detection of AVP in serum and tissue. Further, the AVP-binding peptides can be coupled to a gel matrix. The resulting affinity column can be used to purify AVP from tissue extracts. These above two techniques, used in combination, will enable both the detection and purification of AVP from various sources.

Also included in this invention are addition salts, complexes, or prodrugs such as esters of the compounds of this invention when B is OH, especially the nontoxic pharmaceutically acceptable acid addition salts. The acid addition salts are prepared in standard manner in a suitable solvent from the parent compound and an excess of an acid, such as hydrochloric, hydrobromic, sulfuric, phosphoric, acetic, maleic, succinic, ethanedisulfonic or methanesulfonic acids. The end products of the formula have two strong basic groups in their structures, therefore, their acid addition salt derivatives of the acid forms of the end products, such as the methyl or ethyl esters, are prepared as known to the art. These salts, complexes, or prodrugs are useful as AVP-binding compounds.

DETAILED DESCRIPTION OF THE INVENTION

Figure 1:
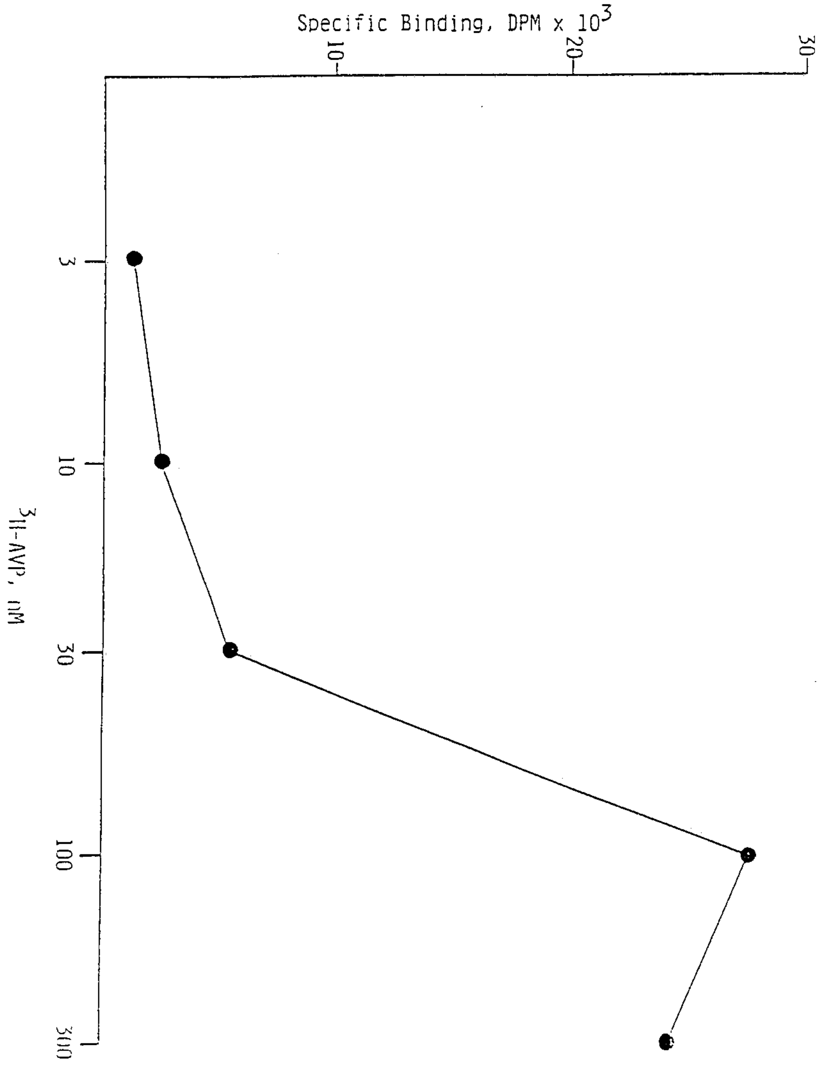
FIG. 1—Specific binding of $^3H$-AVP to AVP-binding peptide Thr-Met-Lys-Val-Leu-Thr-Gly-Ser-Pro. AVP-binding peptide (200 μl of a 2 mg/ml solution) was bound overnight at 4°°C. onto 96-well Immulon plates (Dynatech, Alexandria, Va.). Plates were washed three times with phosphate-buffered saline containing 5% BSA and 0.1% TWEEN™ 20 (binding buffer). Remaining binding sites were bound by incubating plates at room temperature with 20 μl binding buffer/well for 2 hr. After extensive washing, cold AVP (10 μM) was added to the appropriate plates 20 min prior to the addition of $^3H$-AVP. Solid matrix binding was carried out at room temperature for 1 hr. Plates were washed three times and counts were solubilized with 1 N NaOH. Counts were then placed in scintillation vials and counted on a beta-scintillation counter. Specific binding of 3H-AVP was the difference between the binding in the absence and presence of cold AVP.

AVP and its 6-amino acid N-terminus cyclic ring pressinoic acid (PA) are both capable of replacing the interleukin 2 (IL 2) requirement for gamma interferon (IFN γ) production by mouse splenic lymphocytes. We show that the AVP-binding peptide specifically and reversibly blocks AVP help in IFNγ production, but fails to block the helper signal of PA. Thus the intact AVP molecule, and not just the N-terminal cyclic ring, is important for interaction with the binding peptide. AVP interacts with the binding peptide with an apparent $K_D$ of approximately 50 nM. The AVP-binding peptide does not inhibit AVP interaction with its receptor on lymphocytes. Interestingly, while the AVP-binding peptide does not block the PA helper signal for IFN γ induction, the complex of AVP and binding peptide does reversibly block the PA signal. The AVP family of hormones requires conformational flexibility for signal transduction. Thus, we hypothesize that the AVP-binding peptide restricts this flexibility and converts AVP into an antagonist of its own action.

Following are examples which illustrate the process of the invention, including the best mode. These examples should not be construed as limiting. All solvent mixture proportions are by volume unless otherwise noted.

EXAMPLE 1

Ability Of AVP-Binding Peptide To Specifically Block The Helper Signal in IFNγ Production Induction of IFNγ by T-cell mitogens such as staphylococcal enterotoxin A (SEA) requires a T helper signal that is mediated by IL 2 (Torres, B. A., Farrar, W. L. and Johnson, H. M. [1982] J. Immunol. 128:2217–2219). AVP and PA can replace the IL 2 signal (Johnson et al. [1982] supra; Johnson and Torres [1985] supra; and Torres, B. A. and Johnson, H. M. [1988] J. Immunol. 140, April). The ability of peptide Thr-Met-Lys-Val-Leu-Thr-Gly-Ser-Pro to block or inhibit the AVP helper signal for IFNγ production is illustrated for the C57B1/6 mouse spleen cell system in Table 1 (Expt. 1). Removal of helper cells by treatment of spleen cells with anti-Lyt 1.2 antibodies plus complement abrogated competence for IFNγ induction by SEA. AVP and IL 2 restored competence at relatively low concentrations as previously shown (Johnson et al. [1982] supra; and Johnson and Torres [1985] supra). The above peptide blocked restoration of competence by AVP at 100 μM, but had no inhibitory effect on IL 2 help. The blockage of AVP function by the peptide was reversed or overcome by increasing the concentration of AVP in the spleen cell cultures (Table 1, Expt. 2).

The above observations suggest that the peptide blocked AVP function by direct interaction with the hormone. Evidence for such direct interaction is provided by the binding data of FIG. 1, where $^3H$-AVP bound to the peptide coupled to a solid matrix with an apparent $K_D$ of approximately 50 nM. The binding was inhibited by excess cold AVP. We conclude that the peptide blocks AVP function through direct binding to AVP.

TABLE 1

Ability of AVP-binding peptide to specifically block the helper signal in IFN γ production

| Mitogen-stimulated spleen cell cultures | AVP (nM) | IL 2 (U/ml) | Binding peptide (μM) | IFN γ (U/ml ± SD) |
|---|---|---|---|---|
| Expt 1 | | | | |
| Whole | — | — | — | 475 ± 35 |
| Whole | — | — | 150 | 825 ± 35 |
| Helper cell depleted | — | — | — | <3 |
| Helper cell depleted | 10 | — | — | 255 ± 7 |
| Helper cell depleted | 10 | — | 50 | 625 ± 35 |
| Helper cell depleted | 10 | — | 100 | <3 |
| Helper cell depleted | 10 | — | 150 | <3 |
| Helper cell depleted | — | 3 | — | 300 ± 71 |
| Helper cell depleted | — | 3 | 150 | 650 ± 71 |
| Expt 2 | | | | |
| Whole | — | — | — | 120 ± 28 |
| Helper cell depleted | 1000 | — | 100 | <3 |
| Helper cell depleted | 3000 | — | 100 | 350 ± 71 |

Helper cell depletion was carried out as described previously (Johnson et al. [1982] supra). Briefly, C57B1/6 spleen cells (1 ml at 3 to $5\times10^7$ cells/ml), 1 ml of a $10^{-3}$ dilution of monoclonal anti-Lyt 1.2 antibody (New England Nuclear, Boston, Mass.) and guinea pig complement (0.167 ml of serum) were mixed and incubated for 1 hr at 37° C. Cells were then washed twice and viability was determined by trypan blue dye exclusion. Untreated whole spleen cells and anti-Lyt 1.2-treated spleen cells were placed in 24-well plates (Falcon, Oxnard, CA) at a final concentration of $1.5\times10^7$ viable cells/ml in a final volume of 0.3 ml. Experiments were carried out in duplicate and all cultures were induced for IFNγ production with 0.5 μg/ml staphylococcal enterotoxin A (SEA; Toxin Technology, Madison, WI) for 3 days in the presence of synthetic AVP (Peninsula Laboratories, Torrance, Calif.), recombinant human IL 2 (Hoffman-La Roche, Nutley, N.J.), and AVP-binding peptide. Culture supernatants were assayed for IFNγ activity on mouse L cells using vesicular stomatitis virus as described in Langford, M. P., Weigent, D. A., Stanton, G. J., and Baron, S. (1981) Methods in Enzym. 78:339–346. The IFN activity in these cultures was IFNγ as determined by neutralization with specific antisera (Osborne, L. C., Georgiades, J. A., and Johnson, H. M. [1980] Cell Immunol. 53:65–70). AVP-binding peptide was synthesized using a Biosearch 9500 Peptide Synthesizer. Data are representative of at least 5 experiments.

The novel peptides of the invention were synthesized using a Biosearch 9500 Peptide Synthesizer (Biosearch, Inc., San Rafael, Calif.). Also, the novel AVP-binding peptides of the subject invention can be chemically synthesized by solid phase synthetic techniques such as t-BOC and FMOC (Merrifield, R.B. [1963] J. Amer. Chem. Soc. 85:2149; and Chang, C. and Meienhofer, J. [1978] Int. J. Peptide Protein Res. 11:246). The above publications are incorporated herein by reference thereto.

EXAMPLE 2

Effect of Changes in the Amino Acid Sequence of AVP-Binding Peptide on its Ability to Block IFNγ Production The formula for the peptides of the invention is as follows: Thr-Met-X-Val-Leu-Thr-Gly-Ser-Pro-B, wherein X is selected from the group consisting of Lys, Arg and Asp; B is OH, $NH_2$, or NHAlk, wherein Alk is lower alkyl of 1–4 carbons, inclusive. The designations used for the amino acids are those universally used and understood by those skilled in the art.

The peptide initially tested is where X is Lys. As shown in the following Table 2, the arginine-substituted peptide blocked AVP function at the same concentration as the original peptide, while the aspartate-substituted peptide was 50 percent less effective. The valine-substituted peptide did not block AVP function.

TABLE 2

Effect of changes in the amino acid sequence of AVP-binding peptide on its ability to block IFN γ production*

| AVP-binding peptide | Minimal concentration needed to block IFN γ production (μM) |
|---|---|
| Original | 150 |
| $(Arg)^3$ | 150 |
| $(Asp)^3$ | 300 |

TABLE 2-continued

| Effect of changes in the amino acid sequence of AVP-binding peptide on its ability to block IFN γ production* | |
|---|---|
| AVP-binding peptide | Minimal concentration needed to block IFN γ production (μM) |
| $(Val)^3$ | >300 |

*The experiment was carried out as described in Table 1. All peptides were synthesized using a Biosearch 9500 peptide synthesizer. Data are representative of at least 5 experiments.

EXAMPLE 3

Failure of AVP-Binding Peptide to Inhibit Binding of $^3$H-AVP to Receptor on Splenic Lymphocyte The question arises as to whether the AVP-binding peptide inhibits function by blocking interaction of AVP with its receptor on the lymphocyte. As shown in Table 3, AVP-binding peptide at concentrations as high as 10,000 μM had no effect on binding of 300 nM $^3$H-AVP to lymphocyte receptors. By comparison, cold AVP did compete and block $^3$H-AVP binding. As we previously showed (Torres, B. A. and H. M. Johnson [1988] J. Immunol. 140:2179-2183), there are relative low numbers of AVP receptors on lymphocytes and this is reflected by the high ratio of total to specific binding. Thus the AVP-binding peptide blocks AVP function by a mechanism(s) other than inhibition of interaction with receptor.

TABLE 3

Failure of AVP-binding peptide to inhibit binding of $^3$H—AVP to receptor on splenic lymphocyte

| Competitor | Conc. (μM) | DPM (Mean ± SD) |
|---|---|---|
| None | — | 4,965 ± 226 |
| AVP | 0.1 | 5,265 ± 476 |
| | 1.0 | 4,209 ± 150 |
| | 10.0 | 3,621 ± 347 |
| | 100.0 | 3,577 ± 167 |
| AVP-binding peptide | 1,000.0 | 5,489 ± 123 |
| | 10,000.0 | 5,383 ± 450 |

Membranes were prepared as previously described (Torres and Johnson [1988] supra). Freshly dissociated spleen cells were incubated on plastic at 37° C. for 1 hr to remove adherent cells. Plates were washed and non-adherent cells were incubated for an additional hour at 37° C. Washed non-adherent cells were resuspended in 50 mM Tris-HCl buffer (pH 7.4) containing 10 mM EGTA and 10 μM phenylmethylsulfonylfluoride (PMSF), which generally lysed any red blood cells in the preparation. Additional red blood cell lysis was performed using 10 mM potassium bicarbonate buffer containing 16 mM ammonium chloride and 100 μM ethylenediaminetetraacetic acid (EDTA). Cells were washed twice and sonicated on ice using a Fisher Model 300 Sonicator (Fisher Scientific, Pittsburgh, Pa.) with microprobe. Preparations were monitored microscopically and were sonicated until greater than 95% cell rupture was achieved. Sonicated preparations were centrifuged at 1000×g at 4° C. to remove debris and large particles. Supernatants were then spun at 33,000 rpm (55,000×g) at 4° C. for 45 min in a Sorvall UTD65B Ultracentrifuge (T1270 rotor) to isolate membranes. Resulting membrane preparations were resuspended in 50 mM Tris-HCl (ph 7.4) containing 10 mM $MgCL_2$ and 10 μM PMSF, and aliquots were stored at −70° C.

Membranes (30 μg/ml) were incubated in a final volume of 200 μl with cold AVP and/or AVP-binding peptide for 20 min. prior to the addition of 300 nM $^3$H-AVP (specific activity, 70 Ci/mmol; New England Nuclear, Boston, Mass.). Binding was carried out at room temperature for 30 min. at which time samples were placed on ice to stop further binding. Membranes were washed through 0.45 μm filters (GVWP; Millipore, Bedford, MA) presoaked in 2% bovine serum albumin (BSA) with approximately 50× volume of ice cold reaction buffer (50 mM tris-HCl, pH 7.4, 10 mM $MgCl_2$, 2% BSA, 10 μM PMSF). Filters were then placed in scintillation vials and radioactivity was counted on a beta-scintillation counter.

EXAMPLE 4

Failure of AVP-Binding Peptide to Block Pressinoic Acid (PA) Help in IFNγ Production The ability of the AVP-binding peptide to block AVP function, but not block binding to receptor, would suggest that the binding peptide converts AVP into an antagonist of its own action. We tested this hypothesis by first determining the effect of the binding peptide on the PA helper signal for IFNγ production. PA exerts its helper effects on lymphocytes via interaction with the AVP receptor, which on the lymphocyte is novel and different from the $V_1$ receptor on hepatocytes (Torres and Johnson [1988] supra). The AVP-binding peptide failed to block the PA helper signal for IFNγ production while at the same time it blocked that of AVP as illustrated in Table 4. Thus the intact AVP molecule and not the functional PA cyclic ring is required for the blocking effect of the AVP-binding peptide.

TABLE 4

Failure of AVP-binding peptide to block pressinoic acid (PA) help in IFN γ production*

| Mitogen-stimulated spleen cell cultures | Helper peptide (nm) | Binding peptide (μM) | IFN γ (U/ml ± SD) |
|---|---|---|---|
| Whole | — | — | 85 ± 7 |
| Helper cell depleted | — | — | <3 |
| Helper cell depleted | AVP (100) | — | 73 ± 4 |
| Helper cell depleted | AVP (100) | 150 | <3 |
| Helper cell depleted | PA (10) | — | 105 ± 21 |
| Helper cell depleted | PA (10) | 150 | 110 ± 14 |

*Experiment was carried out as described in Table 1. Synthetic PA was purchased from Peninsula Laboratories, Torrance, CA.

EXAMPLE 5

Complex of AVP and AVP-Binding Peptide Blocks Pressinoic Acid (PA) Help in IFNγ Production Having established that the AVP-binding peptide alone cannot block the PA helper signal for IFNγ production, we would predict that the complex of AVP and binding peptide (which binds to the AVP receptor but lacks function) would reversibly block the PA helper signal. This was indeed the case as shown in Table 5, where the complex of AVP and binding peptide blocked PA helper signal for IFNγ production. The blockage was reversed by increasing the concentration of PA. Taken together, the data presented provide compelling evidence that the AVP-binding peptide converts AVP into an antagonist of its own action.

TABLE 5

Complex of AVP and AVP-binding peptide blocks pressinoic acid (PA) help in IFN γ production*

| Mitogen-stimulated spleen cell cultures | PA (nM) | Complex of AVP and binding peptide (nM AVP:μM peptide) | IFN γ (U/ml ± SD) |
|---|---|---|---|
| Whole | — | — | 200 ± 0 |
| Helper cell depleted | — | — | <3 |
| Helper cell depleted | — | 100:150 | <3 |
| Helper cell depleted | 3 | — | <3 |
| Helper cell depleted | 10 | — | 185 ± 21 |
| Helper cell depleted | 30 | — | 250 ± 71 |
| Helper cell depleted | 30 | 100:150 | <3 |
| Helper cell depleted | 300 | 100:150 | <3 |
| Helper cell depleted | 1000 | 100:150 | 240 ± 57 |

*Experiment was carried out as described in Table 1. Equal volumes of AVP (200 nM) and AVP-binding peptide (300 μM) were incubated at room temperature for 1 hr to form the AVP:AVP-binding peptide complex. The complex was added to cultures at the final molar ratio indicated in the table.

EXAMPLE 6

Formulations and Treatment

The compounds of the invention can be used as disclosed in U.S. Pat. No. 4,719,199. Specifically, there can be administered parenterally, or by insufflation, a nontoxic but effective amount of the compound, generally combined with an inert pharmaceutical carrier, to an animal or human in need of treatment to treat edema or to expel water. A suitable dosage of the active ingredient can be from about 5 mcg. to about 10 mg/kg, preferably about 0.1 to about 5 mg/kg, based on a 70 kg patient. The dosage can be applied from about 1 to 5 times daily.

A suitable composition for control or suppression of AVP can be a compound of the invention in the form of a dosage unit, as described above, dissolved or suspended in a standard liquid carrier, for example, isotonic saline contained in ampoule or a suitable vial for use in injection. A suitable composition for insufflation can be administered in a standard metered dose applicator or inhaler. Various other compositions can be used, for example, pulverized powder, oily preparations, gels, buffers for isotonic preparations, emulsions or aerosols. The above compositions and means of administration are all well known in the pharmaceutical art. The diluents and adjuvants used would be compatible and pharmaceutically acceptable. For example, as liquid compositions for oral administration, pharmaceutically acceptable emulsions, solutions, suspensions, syrups or elixirs containing inert diluents, such as water or liquid paraffin, can be used. These compositions can contain substances other than the diluents, e.g., wetting, sweetening, or flavoring products.

The compositions for parenteral administration can be sterile aqueous solutions, or they can be suspensions or emulsions. As a vehicle, polyethylene glycol, a polypropylene glycol, vegetable oils, especially olive oil, and injectable organic esters, e.g., ethyl oleate, can be employed. These compositions can also contain adjuvants, especially wetting agents, emulsifiers, or dispersants.

The compositions for intranasal administration can be sterile aqueous solutions, or they can be suspensions or emulsions, which can optionally be combined with a compatible propellant.

The compositions for rectal administration are suppositories which can contain, in addition to the active product, excipients such as cocoa butter or a semi-synthetic glyceride.

Other suitable formulations of the active peptides in pharmaceutically acceptable diluents or carriers in therapeutic dosage form can be prepared by reference to general texts in the pharmaceutical field. See, for example, *Remington's Pharmaceutical Sciences,* E. Arthur Osol, 16th ed., 1980, Mack Publishing Co., Easton, Pa.

We claim:

1. An AVP-binding peptide having the formula

Thr-Met-X-Val-Leu-Thr-Gly-Ser-Pro-B wherein X is selected from the group consisting of Lys, Arg and Asp; B is OH, $NH_2$ or NHAlk, wherein Alk is lower alkyl of 1–4 carbons, inclusive; or a pharmaceutically acceptable salt or prodrug thereof.

2. The peptide, according to claim 1, wherein X is Lys.

3. The peptide, according to claim 1, wherein X is Arg.

4. The peptide, according to claim 1, wherein X is Asp.

5. A pharmaceutical composition having AVP-binding activity comprising an effective amount of a peptide of the formula Thr-Met-X-Val-Leu-Thr-Gly-Ser-Pro-B wherein X is selected from the group consisting of Lys, Arg and Asp; B is OH, $NH_2$ or NHAlk, wherein Alk is lower alkyl of 1–4 carbons, inclusive; in combination with one or more diluents or adjuvants which are compatible and pharmaceutically acceptable.

6. The composition, according to claim 5, wherein X is Lys.

7. The composition, according to claim 5, wherein X is Arg.

8. The composition, according to claim 5, wherein X is Asp.

* * * * *

UNITED STATES PATENT AND TRADEMARK OFFICE

CERTIFICATE OF CORRECTION

PATENT NO. : 4,786,631

DATED : November 22, 1988

INVENTOR(S) : Howard M. Johnson, Barbara A. Torres

It is certified that error appears in the above-identified patent and that said Letters Patent is hereby corrected as shown below:

Column 2: line 39: "4°°C" should read --4°C--; line 44: "buffer/-well" should read --buffer/well--; line 53: "3H-AVP" should read --$^3$H-AVP--.

Coulmn 6: line 8: "30 min." should read -- 30 min.,--.

Coulmn 7: line 39: "in ampoule" should read --in an ampoule--.

Signed and Sealed this

Ninth Day of May, 1989

*Attest:*

DONALD J. QUIGG

*Attesting Officer* — *Commissioner of Patents and Trademarks*